United States Patent [19]

Berg et al.

[11] Patent Number: 5,194,123

[45] Date of Patent: Mar. 16, 1993

[54] SEPARATION OF 4-METHYL-2-PENTANONE FROM ACETIC ACID BY EXTRACTIVE DISTILLATION WITH DMSO

[75] Inventors: Lloyd Berg, 1314 S. 3rd Ave., Bozeman, Mont. 59715; Marc W. Paffhausen, Bozeman, Mont.

[73] Assignee: Lloyd Berg, Bozeman, Mont.

[21] Appl. No.: 909,175

[22] Filed: Jul. 6, 1992

[51] Int. Cl.$^5$ .................. B01D 3/40; C07C 45/83; C07C 51/44
[52] U.S. Cl. ........................ 203/51; 203/56; 203/57; 203/60; 203/61; 203/62; 203/63; 203/64; 562/608; 568/410
[58] Field of Search ............ 203/57, 51, 56, 60, 203/61, 62, 63, 64; 568/410; 562/608

[56] References Cited

U.S. PATENT DOCUMENTS

| | | | |
|---|---|---|---|
| 2,954,392 | 9/1960 | Rylander | 568/410 |
| 3,013,954 | 12/1961 | Pacoud et al. | 203/62 |
| 3,228,985 | 1/1966 | Carpenter et al. | 568/410 |
| 3,265,592 | 8/1966 | Van Der Weel | 568/410 |
| 4,793,901 | 12/1988 | Berg et al. | 203/57 |
| 4,861,436 | 8/1989 | Berg et al. | 203/38 |
| 4,948,471 | 8/1990 | Berg et al. | 203/57 |

Primary Examiner—Wilbur Bascomb, Jr.

[57] ABSTRACT

4-Methyl-2-pentanone cannot be easily separated from acetic acid by distillation because of the closeness of their boiling points. 4-Methyl-2-pentanone can be readily removed from acetic acid by extractive distillation. Typical effective agents are dimethlsulfoxide (DMSO); DMSO and adipic acid; DMSO, adipic acid and adiponitrile.

1 Claim, No Drawings

SEPARATION OF 4-METHYL-2-PENTANONE FROM ACETIC ACID BY EXTRACTIVE DISTILLATION WITH DMSO

This is a revision of abandoned application Ser. No. 07/569,990 filed Aug. 20, 1990.

FIELD OF THE INVENTION

This invention relates to a method for separating 4-methyl-2-pentanone from acetic acid using DMSO either alone or admixed with other higher boiling organic compounds as the agents in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Acetic acid and 4-methyl-2-pentanone boil only 2.5 Celcius degrees apart and thus have a relative volatility of only 1.06. Table 1 shows the boiling point relationship for these two compounds at 640 mm.HG pressure. From Table 1, it can be seen that in concentrations of 4-methyl-2-pentanone below 77 percent, the boiling point changes only 0.5° C. and further separation by rectification becomes virtually impossible. Although the overall relative volatility is 1.06, in this region it is almost 1.0, just about as difficult to separate as an azeotrope.

TABLE 1

| Boiling Points of 4-Methyl-2-pentanone - Acetic Acid Mixtures at 640 mm. Hg. | | |
|---|---|---|
| % 4-Methyl-2-pentanone | % Acetic Acid | Boiling Point, °C. |
| 100 | 0 | 109 |
| 90 | 10 | 110 |
| 77 | 23 | 111 |
| 50 | 50 | 111.2 |
| 40 | 60 | 111.2 |

TABLE 1-continued

| Boiling Points of 4-Methyl-2-pentanone - Acetic Acid Mixtures at 640 mm. Hg. | | |
|---|---|---|
| % 4-Methyl-2-pentanone | % Acetic Acid | Boiling Point, °C. |
| 33 | 67 | 111.3 |
| 23 | 77 | 111.4 |
| 10 | 90 | 111.4 |
| 0 | 100 | 111.5 |

Extractive distillation would be an attractive method of effecting the separation of 4-methyl-2-pentanone from acetic acid if agents can be found that (1) increase the relative volatility of 4-methyl-2-pentanone to acetic acid and (2) are easy to recover from acetic acid, that is, form no azeotrope with acetic acid and boil sufficiently above acetic acid to make separation by rectification possible with only a few theoretical plates.

Extractive distillation typically requires the addition of an equal amount to twice as much extractive agent as the formic acid-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The object of this invention is to provide a process or method of extractive distillation that will enhance the relative volatility of 4-methyl-2-pentanone from acetic acid in their separation in a rectification column. It is a further object of this invention to identify organic compounds which are stable, can be separated from acetic acid by rectification with relatively few plates and can be recycled to the extractive distillation column and reused with little decomposition.

TABLE 2

| Effective Extractive Distillation Agents Containing DMSO | | | | |
|---|---|---|---|---|
| | Ratios | | Relative Volatilities | |
| Dimethylsulfoxide (DMSO) | 2 | 12/5 | 2.2 | 2.2 |
| DMSO, Acetyl salicylic acid | (1/2)$^2$ | (3/5)$^2$ | 2.3 | 3.3 |
| DMSO, Adipic acid | " | " | 4.4 | 4.0 |
| DMSO, Azelaic acid | " | " | 3.4 | 2.6 |
| DMSO, Benzoic acid | " | " | 2.5 | 2.6 |
| DMSO, 2-Benzoylbenzoic acid | " | " | 3.8 | 3.0 |
| DMSO, p-tertiary Butyl benzoic acid | " | " | 2.9 | 3.4 |
| DMSO, Cinnamic acid | " | " | 2.9 | 2.5 |
| DMSO, Decanoic acid | " | " | 5.4 | 3.5 |
| DMSO, Dodecanedioic acid | " | " | 2.2 | 2.8 |
| DMSO, Glutaric acid | " | " | 3.1 | 2.6 |
| DMSO, Heptanoic acid | " | " | 2.9 | 3.4 |
| DMSO, Hexanoic acid | " | " | 2.1 | 3.2 |
| DMSO, 4-Hydroxybenzoic acid | " | " | 2.2 | 2.2 |
| DMSO, Itaconic acid | " | " | 3.2 | 3.3 |
| DMSO, Malic acid | " | " | 3.5 | 2.8 |

TABLE 2-continued
Effective Extractive Distillation Agents Containing DMSO

| | Ratios | | Relative Volatilities | |
|---|---|---|---|---|
| DMSO, Methyl isoamyl ketone | " | " | 1.6 | 1.6 |
| DMSO, Myristic acid | " | " | 2.7 | 2.0 |
| DMSO, Neodecanoic acid | " | " | 3.9 | 4.4 |
| DMSO, Neopentanoic acid | " | " | 2.0 | 2.5 |
| DMSO, m-Nitrobenzoic acid | " | " | 2.2 | 2.6 |
| DMSO, p-Nitrobenzoic acid | " | " | 1.4 | 2.5 |
| DMSO, Octanoic acid | " | " | 3.1 | 2.5 |
| DMSO, Oxalic acid | " | " | 4.1 | 4.6 |
| DMSO, Diethylene glycol diethyl ether | " | " | 1.2 | 1.2 |
| DMSO, Salicylic acid | " | " | 2.1 | 2.6 |
| DMSO, Sebacic acid | " | " | 2.3 | 2.3 |
| DMSO, Succinic acid | " | " | 2.5 | 2.7 |
| DMSO, o-Toluic acid | " | " | 2.6 | 2.6 |
| DMSO, m-Toluic acid | " | " | 2.6 | 3.0 |
| DMSO, p-Toluic acid | " | " | 2.1 | 2.5 |
| DMSO, 3,4,5-Trimethyoxybenzoic acid | " | " | 3.5 | 3.2 |
| DMSO, Undecanoic acid | " | " | 2.2 | 2.1 |
| DMSO, Acetyl salicylic acid, Acetophenone | $(1/3)^3$ | $(2/5)^3$ | 1.9 | 2.7 |
| DMSO, Adipic acid, Adiponitrile | " | " | 3.2 | 3.3 |
| DMSO, Azelaic acid, Diisobutyl ketone | " | " | 2.0 | 2.2 |
| DMSO, Benzoic acid, Anisole | " | " | 1.7 | 1.7 |
| DMSO, 2-Benzoylbenzoic acid, Glycerol triacetate | " | " | 2.1 | 1.3 |
| DMSO, p-tert. Butyl benzoic acid, Methyl salicylate | " | " | 1.7 | 1.5 |
| DMSO, Cinnamic acid, Butyl ether | " | " | 1.6 | 1.8 |
| DMSO, Decanoic acid, Cyclohexanone | " | " | 2.8 | 2.5 |
| DMSO, Dodecanedioic acid, Diisobutyl ketone | " | " | 2.0 | 2.0 |
| DMSO, Glutaric acid, Methyl isoamyl ketone | $(1/3)^3$ | $(2/5)^3$ | 1.7 | 1.4 |
| DMSO, Heptanoic acid, Ethyl benzoate | " | " | 2.6 | 2.3 |
| DMSO, Hexanoic acid, Methyl benzoate | " | " | 1.8 | 1.9 |
| DMSO, 4-Hydroxybenzoic acid, Ethylene glycol diacetate | " | " | 1.9 | 1.9 |
| DMSO, Itaconic acid, 2-Octanone | " | " | 2.2 | 2.2 |
| DMSO, Malic acid, Diethylene glycol dibenzoate | " | " | 2.8 | 2.2 |
| DMSO, Myristic acid, Hexyl acetate | " | " | 2.2 | 2.6 |
| DMSO, Neodecanoic acid, Isophorone | " | " | 3.1 | 3.9 |
| DMSO, Neopentanoic acid, 2-Heptanone | " | " | 2.0 | 2.1 |
| DMSO, m-Nitrobenzoic acid, Benzyl acetate | " | " | 1.7 | 1.4 |
| DMSO, p-Nitrobenzoic acid, Isobutyl heptyl ketone | " | " | 1.1 | 1.4 |
| DMSO, Octanoic acid, Butyl benzoate | " | " | 2.4 | 2.0 |
| DMSO, Oxalic acid, 2-Octanone | " | " | 2.1 | 3.1 |
| DMSO, Undecanoic acid, Benzyl benzoate | " | " | 2.9 | 2.5 |
| DMSO, Salicylic acid, Ethyl salicylate | " | " | 1.9 | 1.6 |
| DMSO, Sebacic acid, Ethyl butyl ketone | " | " | 1.8 | 1.9 |
| DMSO, Succinic acid, 2-Undecanone | " | " | 1.7 | 1.8 |
| DMSO, o-Toluic acid, Diethylene glycol dimethyl ether | " | " | 1.9 | 2.2 |
| DMSO, m-Toluic acid, Diethylene glycol diethyl ether | " | " | 1.6 | 2.0 |
| DMSO, p-Toluic acid, Dipropylene glycol dibenzoate | " | " | 2.1 | 1.2 |
| DMSO, 3,4,5-Trimethyoxybenzoic acid, Ethyl phenyl acetate | " | " | 3.6 | 2.6 |
| DMSO, Undecanoic acid, Diethyl maleate | " | " | 1.7 | 1.1 |

TABLE 3
Data From Run Made In Rectification Column

| Agent | Column | Time, hrs. | Weight % 4-Me-2-Pt | Weight % Acetic Acid | Relative Volatility |
|---|---|---|---|---|---|
| 50% DMSO, 50% Methyl isoamyl ketone | Overhead | 0.5 | 23.9 | 76.1 | 1.25 |
| | Bottoms | | 8.8 | 91.2 | |
| 50% DMSO, 50% Methyl isoamyl ketone | Overhead | 1 | 47.4 | 52.6 | 1.25 |
| | Bottoms | | 21.7 | 78.3 | |

SUMMARY OF THE INVENTION

The objects of the invention are provided by a process for separating 4-methyl-2-pentanone from acetic acid which entails the use of dimethylsulfoxide (DMSO), either alone or admixed with higher boiling organic compounds as the agent in extractive distillation.

DETAILED DESCRIPTION OF THE INVENTION

We have discovered that dimethylsulfoxide (DMSO), either alone or admixed with other high boiling organic compounds, will effectively increase the relative volatility of 4-methyl-2-pentanone to acetic acid and permit the separation of 4-methyl-2-pentanone from acetic acid by rectification when employed as the agent in extractive distillation. Table 2 lists DMSO and its mixtures and the approximate proportions that we have found to be effective. The data in Table 2 was obtained in a vapor-liquid equilibrium still. In each case, the starting material was a 50-50 wt. % mixture of 4-methyl-2-pentanone and acetic acid. The ratios are the parts by weight of extractive agent used per part of 4-methyl-2-pentanone-acetic acid mixture. The relative volatilities are listed for each of the two ratios employed. The compounds which are effective when used in mixtures with DMSO are acetyl salicylic acid, adipic acid, azelaic acid, benzoic acid, 2-benzoylbenzoic acid, p-tertiary butyl benzoic acid, cinnamic acid, decanoic acid, dodecanedioic acid, glutaric acid, heptanoic acid, hexanoic acid, 4-hydroxybenzoic acid, itaconic acid, malic acid, myristic acid, neodecanoic acid, neopentanoic acid, m-nitrobenzoic acid, p-nitrobenzoic acid, octanoic acid, oxalic acid, salicylic acid, sebacic acid, succinic acid, o-toluic acid, m-toluic acid, p-toluic acid, 3,4,5-trimethoxybenzoic acid, undecanoic acid, acetophenone, adiponitrile, methyl isoamyl ketone, diethylene glycol diethyl ether, diisobutyl ketone, anisole, glycerol triacetate, methyl salicylate, butyl ether, cyclohexanone, ethyl benzoate, methyl benzoate, ethylene glycol diacetate, 2-octanone, diethylene glycol dibenzoate, hexyl acetate, isophorone, 2-heptanone, benzyl acetate, isobutyl heptyl ketone, butyl benzoate, benzyl benzoate, ethyl salicylate, ethyl butyl ketone, 2-undecanone, diethylene glycol dimethyl ether, dipropylene glycol dibenzoate, ethyl phenyl acetate and diethyl maleate.

The two relative volatilities shown in Table 2 correspond to the two different ratios investigated. For example, in Table 2 two parts of DMSO mixed with one part of 4-methyl-2-pentanone-acetic acid mixture give a relative volatility of 2.2, 12/5 parts of DMSO also give 2.2. One half part of DMSO mixed with one half part of adipic acid with one part of the 4-methyl-2-pentanone-acetic acid mixture give a relative volatility of 4.4, 3/5 parts of DMSO plus 3/5 parts of adipic acid give 4.0. One third part of DMSO plus ⅓ part of adipic acid plus ⅓ part of adiponitrile with one part of the 4-methyl-2-pentanone-acetic acid mixture gives a relative volatility of 3.2, with 2/5 parts, these three give a relative volatility of 3.3. In every example in Table 2, the starting material is a 4-methyl-2-pentanone-acetic acid mixture which possesses a relative volatility of about 1.11.

One of the mixtures, DMSO-methyl isoamyl ketone, listed in Table 2 and whose relative volatility had been determined in the vapor-liquid equilibrium still, was then evaluated in a glass perforated plate rectification column possessing 5.3 theoretical plates and the results listed in Table 3. The data in Table 3 was obtained in the following manner. The charge was 200 grams of 50% 4-methyl-2-pentanone–50% acetic acid and after a half hour of operation in the 5.3 theoretical plate column to establish equilibrium, a mixture containing 50% DMSO–50% methyl isoamyl ketone at 85° C. and 20 ml/min. was pumped in. The rectification was continued with sampling of overhead and bottoms after ½ hour. The analysis is shown in Table 3 and was 23.9% 4-methyl-2-pentanone, 76.1% acetic acid in the overhead and 8.8% 4-methyl-2-pentanone, 91.2% acetic acid in the bottoms which gives a relative volatility of 1.25 of 4-methyl-2-pentanone to acetic acid. After one hour of continuous operation, the overhead was 47.4% 4-methyl-2-pentanone, 52.6% acetic acid, the bottoms was 21.7% 4-methyl-2-pentanone, 78.3% acetic acid which is a relative volatility of 1.25.

THE USEFULNESS OF THE INVENTION

The usefulness or utility of this invention can be demonstrated by referring to the data presented in Tables 1, 2 and 3. All of the successful extractive distillation agents show that 4-methyl-2-pentanone and acetic acid can be separated from their mixtures by means of distillation in a rectification column and that the ease of separation as measured by relative volatility is considerable. Without these extractive distillation agents little improvement will occur in the rectification column. The data also show that the most attractive agents will operate at a boilup rate low enough to make this a useful and efficient method of recovering high purity 4-methyl-2-pentanone from any mixture with acetic acid. The stability of the compounds used and the boiling point difference is such that complete recovery and recycle is obtainable by a simple distillation and the amount required for makeup is small.

WORKING EXAMPLES

Example 1: Forty grams of a 4-methyl-2-pentanone-acetic acid mixture and 40 grams DMSO were charged to a vapor-liquid equilibrium still and refluxed for four hours. Analysis indicated a vapor composition of 15.6% 4-methyl-2-pentanone, 84.4% acetic acid, a liquid composition of 9.8% 4-methyl-2-pentanone, 92.2% acetic acid which is a relative volatility of 2.2.

Example 2: Eighty grams of a 4-methyl-2-pentanone-acetic acid mixture, 25 grams of DMSO and 25 grams of adipic acid were charged to the vapor-liquid equilibrium still and refluxed for 16 hours. Analysis indicated a vapor composition of 36.4% 4-methyl-2-pentanone, 63.6% acetic acid, a liquid composition of 11.3% 4-methyl-2-peantanone, 88.7% acetic acid which is a relative volatility of 4.4. Five grams of DMSO and five grams of adipic acid were added and refluxing continued for another six hours. Analysis indicated a vapor composition of 28.2% 4-methyl-2-pentanone, 71.8% acetic acid, a liquid composition of 9% 4-methyl-2-pentanone, 91% acetic acid which is a relative volatility of 4.0.

Example 3: Eighty grams of a 4-methyl-2-pentanone-acetic acid mixture, 17 grams of DMSO, 17 grams of adipic acid and 17 grams of adiponitrile were charged to the vapor-liquid equilibrium still and refluxed for seventeen hours. Analysis indicated a vapor composition of 28.8% 4-methyl-2-pentanone, 71.2% acetic acid, a liquid composition of 11.1% 4-methyl-2-pentanone, 88.9% acetic acid which is a relative volatility of 3.2. Three grams each of DMSO, adipic acid and adiponitrile were added and refluxing continued for another six hours. Analysis indicated a vapor composition of 25.9% 4-methyl-2-pentanone, 74.1% acetic acid, a liquid composition of 9.6% 4-methyl-2-pentanone, 90.4% acetic acid which is a relative volatility of 3.3.

Example 4: A glass perforated plate rectification column was calibrated with ethylbenzene and p-xylene which possesses a relative volatility of 1.06 and found to have 5.3 theoretical plates. A solution comprising 100 grams of 4-methyl-2-pentanone and 100 grams of acetic acid was placed in the stillpot and heated. When refluxing began, an extractive agent comprising 50% DMSO and 50% methyl isoamyl ketone was pumped into the column at a rate of 20 ml/min. The temperature of the extractive agent as it entered the column was 85° C. After establishing the feed rate of the extractive agent, the heat input to the 4-methyl-2-pentanone and acetic acid in the stillpot was adjusted to give a total reflux rate of 10–20 ml/min. After one half hour of operation, the overhead and bottoms samples of approximately two ml. were collected and analysed by gas chromatography. The overhead analysis was 23.9% 4-methyl-2-pentanone, 76.1% acetic acid. The bottoms analysis was 8.8% 4-methyl-2-pentanone, 91.2% acetic acid. Using these compositions in the Fenske equation, with the number of theoretical plates in the column being 5.3, gave an average relative volatility of 1.25 for each theoretical plate. After one hour of total operating time, the overhead and bottoms samples were again taken and analysed. The overhead composition was 47.4% 4-methyl-2-pentanone, 52.6% acetic acid and the bottoms composition was 21.7% 4-methyl-2-pentanone, 78.3% acetic acid. This gave an average relative volatility of 1.25 for each theoretical plate. These data are presented in Table 3.

We claim:
1. A method for recovering 4-methyl-2-pentanone from mixtures of 4-methyl-2-pentanone and acetic acid which comprises distilling a mixture of 4-methyl-2-pentanone and acetic acid in a rectification column in the presence of about one part of an extractive agent per part of 4-methyl-2-pentanone-acetic acid mixture, recovering the 4-methyl-2-pentanone as overhead prod- uct and obtaining the acetic acid and the extractive agent from the stillpot, wherein said extractive agent comprises dimethyl sulfoxide and at least one material selected from the group consisting of p-nitrobenzoic acid, succinic acid, 3,4,5-trimethoxybenzoic acid, diisobutyl ketone, hexyl acetate, diethylene glycol dibenzoate, isobutyl heptyl ketone, ethyl butyl ketone and 2-undecanone.

* * * * *